United States Patent [19]

Tsuchiya et al.

[11] Patent Number: 5,677,444

[45] Date of Patent: Oct. 14, 1997

[54] METHOD FOR THE PREPARATION OF β-KETOTHIOAMIDE COMPOUND

[75] Inventors: Tohru Tsuchiya; Isao Shibuya; Yoichi Taguchi; Akihiro Oishi; Kazumasa Honda, all of Tsukuba, Japan

[73] Assignee: Japan as represented by Director General of Agency of Industrial Science and Technology, Tokyo, Japan

[21] Appl. No.: 530,402

[22] Filed: Sep. 15, 1995

[30] Foreign Application Priority Data

Sep. 28, 1994 [JP] Japan ................................ 6-232846

[51] Int. Cl.$^6$ ...................... C07C 327/42; C07D 223/08; C07D 225/02

[52] U.S. Cl. ..................... 540/451; 540/454; 540/488; 540/526; 540/529; 540/533; 556/427; 556/433; 564/74; 564/78

[58] Field of Search ....................... 540/451, 529, 540/533; 564/74, 78; 556/427, 433

[56] References Cited

PUBLICATIONS

Schaumann, The Chemistry of Thioketens, Tetrahedron, vol. 44, No. 7, pp. 1827–1871, 1988.
Harris et al., Bistrimethylsilylthioketen: a versatile reagent for thioketen–based syntheses, J. Chem. Soc., Chem. Comm., (24) pp. 1008–1009 (1976).
Schroth et al., 2,4,6–Tris(dialkylamino)pyrilium salts and related systems, synthesis and reactions behaviour, Tetrahedron Letters, vol. 29, No. 37, pp. 4695–4698 (1988).

*Primary Examiner*—Mukund J. Shah
*Assistant Examiner*—Deepak R. Rao
*Attorney, Agent, or Firm*—Wenderoth, Lind & Ponack

[57] ABSTRACT

A novel and simple method is proposed for the synthetic preparation of an N,N-disubstituted β-ketothioamide compound represented by the general formula $$R^1R^2N-CS-CH_2-CO-R^3,$$

in which $R^1$ and $R^2$ are each a monovalent hydrocarbon group or each a divalent hydrocarbon group jointly forming a cyclic structure together with the nitrogen atom and $R^3$ is a hydrogen atom, a monovalent hydrocarbon group or a divalent hydrocarbon group forming a cyclic structure jointly with $R^1$, $R^1$ being a divalent hydrocarbon group and $R^2$ being a monovalent hydrocarbon group. The method comprises: (a) mixing an N,N-disubstituted amide compound represented by the general formula $$R^1R^2N-CO-R^3,$$

and a bis(trialkylsilyl)thioketene compound represented by the general formula $$(R_3Si)_2C=C=S,$$

in which each R is an alkyl group, to effect an addition reaction therebetween forming an intermediate compound; and (b) dissolving the intermediate compound obtained in step (a) in an alcohol.

6 Claims, 1 Drawing Sheet

METHOD FOR THE PREPARATION OF β-KETOTHIOAMIDE COMPOUND

BACKGROUND OF THE INVENTION

The present invention relates to a synthetic method for the preparation of a β-ketothioamide compound or, more particularly, relates to a synthetic method for the preparation of an N,N-disubstituted β-ketothioamide compound by utilizing a novel synthetic route.

By virtue of the unique chemical structure, N,N-disubstituted β-ketothioamide compounds are each a compound expected to have an activity as a chelating agent specifically to form a chelate compound with atoms of a transition metal such as copper, nickel and the like. Nevertheless, no reliable synthetic method for the preparation of these compounds has been developed in the prior art, although such a compound could be prepared, as a possible approach, by the reaction of a β-ketoacid halide and a secondary amine or by the reaction of an N,N-disubstituted thiocarbamoyl halide and an acetylated compound in the enol form, presumably, due to the low availability of the starting reactants or the low reaction velocity.

Japanese Patent Kokai 5-246980 recently published discloses a large number of β-oxo-β-benzene propane thioamide derivatives having the same skeletal structure as the above mentioned β-ketothioamide compound which can be expected to have various pharmaceutical activities. Reportedly, these N,N-disubstituted β-ketothioamide compounds are prepared by the synthetic route of the reaction between an acetophenone compound and an isocyanate compound or the reaction between a dithioester compound and a corresponding amine compound. These methods, however, have a problem in the versatility for the preparation of various N,N-disubstituted β-ketothioamide compounds.

SUMMARY OF THE INVENTION

The present invention accordingly has an object to provide a novel, versatile and efficient method for the preparation of an N,N-disubstituted β-ketothioamide compound including those not known in the prior art or those which cannot be synthesized by the above described prior art methods.

Thus, the present invention provides a novel synthetic method for the preparation of an N,N-disubstituted β-ketothioamide compound represented by the general formula $$R^1R^2N-CS-CH_2-CO-R^3, \quad (I)$$

in which $R^1$ and $R^2$ are each a monovalent hydrocarbon group or each a divalent hydrocarbon group jointly forming a cyclic structure together with the nitrogen atom and $R^3$ is a hydrogen atom, a monovalent hydrocarbon group or a divalent hydrocarbon group forming a cyclic structure jointly with $R^1$, $R^1$ being a divalent hydrocarbon group and $R^2$ being a monovalent hydrocarbon group, which comprises the steps of:

(a) mixing an N,N-disubstituted amide compound represented by the general formula $$R^1R^2N-CO-R^3, \quad (II)$$

in which each symbol has the same meaning as defined above, and a bis(trialkylsilyl)thioketene compound represented by the general formula $$(R_3Si)_2C=C=S, \quad (III)$$

in which each R is, independently from the others, an alkyl group, to effect an addition reaction therebetween forming an intermediate compound; and (b) dissolving the intermediate compound obtained in step (a) in an alcohol.

DETAILED DESCRIPTION OF THE PREFERRED EMBODIMENTS

Figure 1:
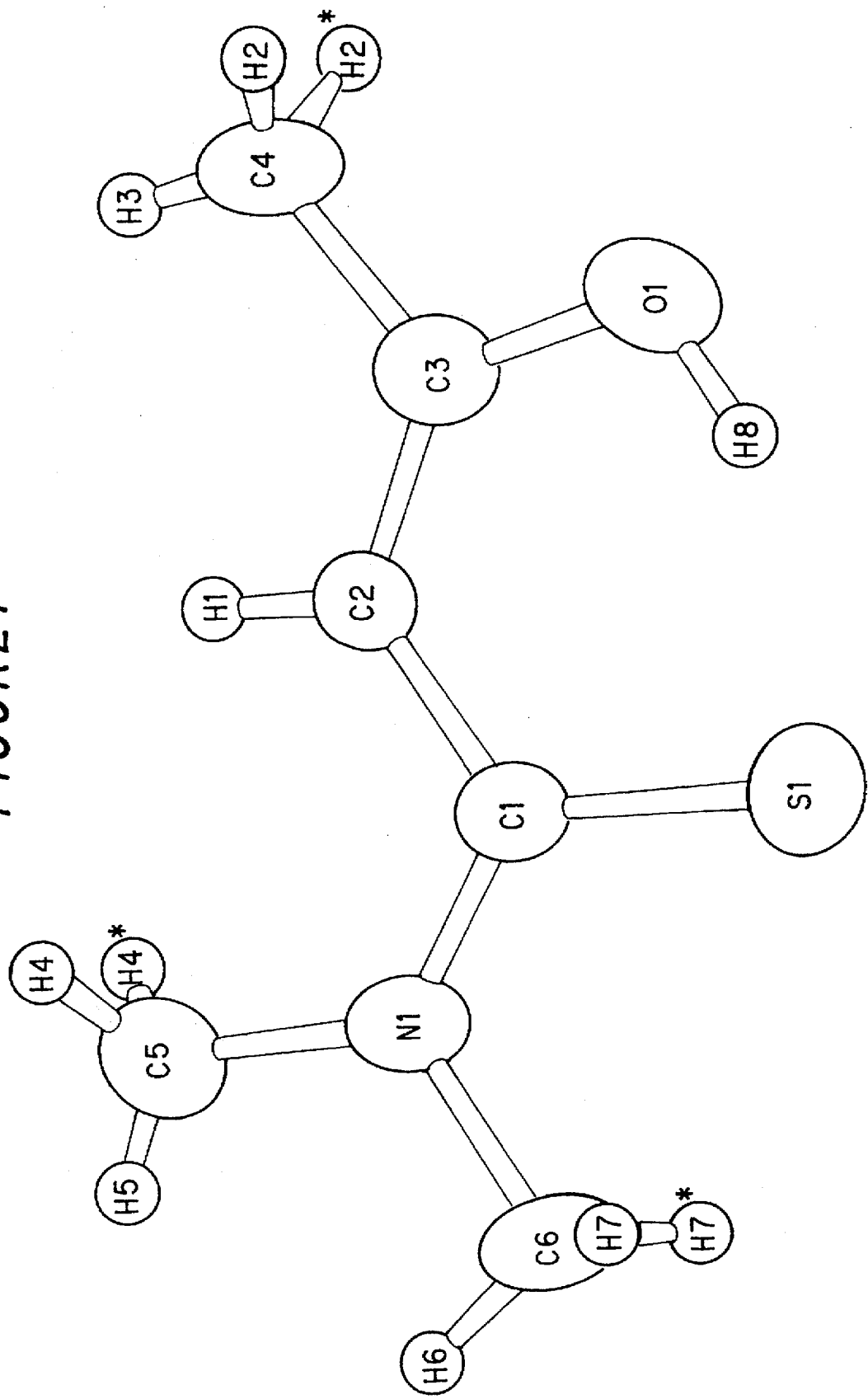
FIG. 1 is an ORTEP diagram of N,N-dimethyl-3-oxothiobutyramide prepared in Example 1.

As is described above, the synthetic process according to the inventive method proceeds in two steps including step (a), in which the two reactants are reacted to form an addition product having trialkylsilyl groups in a molecule as an intermediate compound, and step (b), in which the addition product obtained in step (a) is dissolved in an alcohol so as to effect a kind of alcoholysis reaction of the trialkylsilyl groups. This inventive method is so versatile that a variety of N,N-disubstituted β-ketothioamide compounds of the general formula (I) which are novel compounds not known in the prior art nor reported in any literatures but having usefulness not only as a chelating agent for various transition metal atoms such as copper, nickel and the like but also as an intermediate for the synthetic preparation of various kinds of thioamide compounds depending on the combination of the groups denoted by $R^1$, $R^2$ and $R^3$.

In step (a) of the inventive method, an N,N-disubstituted amide compound of the general formula (II) and the bis(trialkylsilyl)thioketene compound of the general formula (III) are mixed together to form a reaction mixture in which the addition reaction proceeds between the reactants to give an addition product as the intermediate compound. In the general formula (II) representing the N,N-disubstituted amide compound, $R^1$ and $R^2$ are each, independently from the other, a monovalent hydrocarbon group exemplified by aliphatic hydrocarbon groups, alicyclic hydrocarbon groups and aromatic hydrocarbon groups. Particular examples of these monovalent hydrocarbon groups include alkyl groups having 1 to 10 carbon atoms such as methyl, ethyl, propyl, isopropyl, butyl, isobutyl, pentyl, isopentyl, hexyl, nonyl and decyl groups, alkenyl groups such as vinyl, allyl and pentenyl groups, cycloalkyl groups such as cyclopentyl and cyclohexyl groups, aryl groups such as phenyl and naphthyl groups and aralkyl groups such as benzyl and 2-phenylethyl groups as well as those substituted hydrocarbon groups obtained by replacing a part or all of the hydrogen atoms in the above named unsubstituted hydrocarbon groups with one or more of substituents such as halogen atoms, alkoxy groups, alkylthio groups, disubstituted amino groups, acyl groups and the like. Alternatively, $R^1$ and $R^2$ are each, independently from the other, a divalent hydrocarbon group jointly forming a heterocyclic structure together with the nitrogen atom to which each of $R^1$ and $R^2$ is bonded. In this case, $R^1$ and $R^2$ can be bonded either directly or with intervention of a divalent atom or group such as —O—, —S— and the like to form a heterocyclic ring.

On the other hand, $R^3$ in the general formula (II) is a hydrogen atom or a monovalent hydrocarbon group which can be exemplified by those given above as the examples of the monovalent hydrocarbon groups denoted by $R^1$ and $R^2$. Alternatively, $R^3$ can be a divalent hydrocarbon group forming a cyclic structure jointly with $R^1$, which is necessarily a divalent hydrocarbon group, together with the linkage of =N—CO— while $R^2$ is a monovalent hydrocarbon group.

Particular examples of the N,N-disubstituted amide compound suitable as one of the starting reactants in the inventive method include N,N-dimethyl acetamide, N,N-diethyl acetamide, N,N-dipropyl acetamide, N-methyl-N-ethyl acetamide, N,N-dimethyl propionamide, N,N-diethyl propionamide, N,N-dipropyl propionamide, N,N-dimethyl butyramide, N,N-diethyl butyramide, N,N-dimethyl pentanamide, N,N-diethyl pentanamide, N,N-dimethyl benzamide, N,N-diethyl benzamide, N,N-dimethylphenyl acetamide, N,N-diethylphenyl acetamide, N,N-dimethyl cinnamamide, N-acetyl pyrrolidine, N-acetyl piperidine, N-acetyl morpholine, N-benzoyl pyrrolidine, 1-methyl pyrrolidin-2-one, N-methyl-ε-caprolactam and the like.

The other reactant to be reacted with the above described N,N-disubstituted amide compound of the general formula (II) is a bis(trialkylsilyl)thioketene compound of the general formula (III), in which each R is, independently from the others, an alkyl group. Examples of the bis(trialkylsilyl) thioketene compound suitable as the reactant in the inventive method include bis(trimethylsilyl) thioketene, bis (triethylsilyl)thioketene, bis(tripropylsilyl)thioketene, trimethylsilyl triethylsilyl thioketene, bis (dimethylethylsilyl)thioketene, bis(methyldiethylsilyl) thioketene and the like.

It is usual that the reaction mixture for step (a) of the inventive method is prepared by mixing the N,N-disubstituted amide compound and the bis(trialkylsilyl) thioketene compound in such a molar proportion that the amount of the former reactant is in some excess over stoichiometry relative to the latter reactant. The reaction of step (a) proceeds by merely keeping the mixture at room temperature and the reaction is usually complete within several hours to several days. It is optional to heat the mixture at a temperature of 40° to 60° C., especially, when the miscibility of the reactant compounds is low at room temperature. Although use of a solvent as a diluent of the reaction mixture is undesirable in most cases because of possible retardation of the reaction velocity, it is optional to use a small volume of an organic solvent when the miscibility of the reactant compounds is low or when the reaction is too violent. The organic solvent, which must be non-reactive with the reactant compounds, is selected preferably from ether compounds. Completion of the reaction can be confirmed by finding disappearance of the bis(trialkylsilyl) thioketene compound in the reaction mixture, for example, by the gas chromatographic analysis.

The intermediate compound obtained in step (a) of the inventive method is a 1:1 addition product of the reactant compounds. It is not always necessary to isolate this intermediate compound from the reaction mixture by a suitable method such as distillation and sublimation but the reaction mixture containing the intermediate compound can be as such subjected to step (b) of the inventive method. In step (b) of the inventive method, the intermediate compound obtained in step (a) is, either isolated from or contained in the reaction mixture, is dissolved in an alcohol to effect the desilylation or protonation reaction. The amount of the alcohol to dissolve the intermediate compound is preferably about 5 times by volume based on the intermediate compound per se or the reaction mixture containing the same. The alcohol is selected from aliphatic lower alcohols having 1 to 4 carbon atoms in a molecule, of which methyl alcohol is preferred. The reaction with the alcohol can be accelerated catalytically by the addition of a small amount of an acid, which may be an inorganic acid, organic acid or solid acid, to the alcohol solution of the intermediate compound. The acid catalyst is selected in consideration of removability after completion of the reaction by distillation or filtration. In particular, hydrogen chloride is preferable which is used in an amount of 0.005 to 0.05% by weight based on the alcohol. Completion of the desilylation or protonation reaction can be confirmed by finding disappearance of the intermediate compound in the alcohol solution, for example, by the gas chromatographic analysis.

After completion of the alcoholysis reaction, the desired reaction product can be isolated from the alcoholic solution in the form of a crude product by removing the alcohol and the trialkyl alkoxy silane as the by-product by distillation, preferably, under reduced pressure. The thus obtained crude β-ketothioamide compound can be purified by a suitable purification method such as distillation or sublimation, when the vapor pressure of the compound is high enough, or by the column chromatographic method using a column of silica gel or alumina. When the intermediate compound as the starting material in step (b) has a sufficiently high purity as being isolated from the reaction mixture in step (a) followed by thorough purification, a β-ketothioamide compound having a good purity can be obtained in an almost quantitative yield only by removing the excess of the alcohol and the trialkyl alkoxy silane compound as the by-product from the alcoholic solution after step (b) without undertaking any further purification procedure. It should be noted that the β-ketothioamide compounds in general exhibit the proton tautomerism so that the keto form compound of the general formula (I) is present in a solution as an equilibrium mixture with the corresponding enol form as one of the proton tautomers and the compound cannot be isolated in a pure form of one of the tautomers unless the isolation procedure is undertaken under special conditions therefor.

The above described method of the invention comprising the steps (a) and (b) is applicable to the preparation of not only the β-ketothioamide compounds having a straightly linear molecular structure such as N,N-dimethyl-3-oxothiobutyramide, N,N-dimethyl-3-oxothiopentanamide, N,N-dimethyl-3-oxo-3-phenylthiopropionamide and the like but also those having a cyclic structure such as N-methyl-3-oxo-ε-thiocaprolactam, 1-aza-1-methyl-2-thioxo-4-cyclononanone and the like.

The β-ketothioamide compounds obtained by the above described inventive method are each a novel compound not known in the prior art nor reported in any literatures and can be identified by the methods of nuclear magnetic resonance spectroscopy ($^1$H-NMR and $^{13}$C-NMR), mass spectrometry (MS), X-ray crystallographic analysis and elementary analysis.

Though not fully clear, the reactions in steps (a) and (b) of the inventive method proceed presumably according to the following reaction equations:

Step (a):

$R^1R^2N-CO-R^3$ + $(R_3Si)_2C=C=S$ ⟶ $(R_3Si)C(=C=S)C(NR^1R^2)R^3-OSiR_3$ (II)　　　　　　(III)　　　　　　　　　　(IV)

Step (b):

$R^1R^2N-CS-CH_2-CO-R^3$ (I)

⬆⬇　　　　⬅── $R^1R^2N-CS-C(SiR_3)=CR^3-OSiR_3$ (IV')

$R^1R^2N-CS-CH=C(OH)R^3$ (I')

in which each symbol has the same meaning as defined before.

As is understood from the above proposed reaction equations, the reaction in step (a) is an addition reaction of the trialkylsilyl group and the trialkylsilyl thioketene residue derived from the bis(trialkylsilyl)thioketene compound (III) to the carbonyl O and carbonyl C, respectively, of the N,N-disubstituted amide compound (II) to give the intermediate compound (IV) which is transformed by intramolecular rearrangement to the compound (IV'). In step (b) of the inventive method, the compound (IV') is dissolved in an alcohol and subjected to an alcoholysis reaction to give the compound of the formula (I') which is the enol form of the desired β-ketothioamide compound (I) in the keto form in tautomeric equilibrium with the enol form (I'). Since the intramolecular rearrangement reaction from (IV) to (IV') is little affected by the substituent groups $R^1$ and $R^2$ on the nitrogen atom and $R^3$ on the carbonyl group, the inventive method is very versatile for the preparation of a large number of the β-ketothioamide compounds with a great variety relative to the combination of these substituent groups. Accordingly, the practical usefulness of the compounds prepared by the inventive method is not limited to a chelating agent as is readily understood from the high chelating activity of an analogous β-ketothiocarbonyl compound such as 4-thioxo-2-pentanone for various kinds of metal ions but the compounds are useful as an intermediate for the synthesis of various compounds having pharmaceutical or biological activities. In particular, the inventive method provides a novel and very convenient route for the synthesis of a cyclic ketothioamide compound starting from an amide compound of the general formula (II) having a cyclic structure formed by the linkage between the groups $R^1$ and $R^3$, each being a divalent hydrocarbon group, and containing carbon atoms in number smaller by 2 than in the final compound.

In the following, examples are given to illustrate the method of the invention in more detail although the scope of the present invention is never limited by these examples.

EXAMPLE 1

A liquid mixture was prepared in a glass vessel from 0.50 g (2.5 mmoles) of bis(trimethylsilyl) thioketene and 0.24 g (2.8 mmoles) of N,N-dimethyl acetamide and the mixture was kept standing at room temperature for 48 hours so that the mixture was found to be converted into a solid. The thus obtained solid was transferred into a sublimation tube which was evacuated to a reduced pressure of 0.05 mmHg at 60° C. to obtain 0.46 g of a sublimate which could be identified to be the addition product of the general formula (IV) or (IV') shown above in which $R^1$, $R^2$, $R^3$ and R are each a methyl group from the results of the elementary analysis shown below. The calculated values are for the molecular formula of $C_{12}H_{27}ONSSi_2$. The yield of this intermediate compound was 65% of the theoretical value.

Elementary analysis:

|  | C | H | N | S |
|---|---|---|---|---|
| Calculated, % | 49.77 | 9.40 | 4.84 | 11.07 |
| Found, % | 49.91 | 9.52 | 4.99 | 10.86 |

In the next place, 0.3 g of this intermediate compound was dissolved in 5 ml of methyl alcohol containing 0.01% by weight of hydrogen chloride to form a solution, of which an increase in the temperature was noted due to evolution of the heat of reaction. Thereafter, the solution was subjected to stripping under reduced pressure to remove the volatile matters including methyl alcohol and trimethyl methoxy silane and the residue was dissolved in diethyl ether to give a solution from which the diethyl ether was allowed to spontaneously evaporate leaving 0.14 g of a crystalline solid which could be identified to be N,N-dimethyl-3-oxothiobutyramide of the formula $Me_2N-CS-CH_2-CO-Me$, in which Me is a methyl group, from the results of the analyses shown below. The yield of this product was 94% based on the intermediate compound and the overall yield was 61% of the theoretical values. This compound after recrystallization from ethyl alcohol had a melting point ranging in the range from 87.6° to 97.6° C. presumably due to the tautomerism between the keto and enol forms. Formation of a chelate compound was confirmed between this compound and divalent metal ions of copper or nickel in methyl alcohol.

MS: m/z =145 (M+) (calculated value 145 for $C_6H_{11}ONS$)

$^1$H-NMR: 14.98 ppm (s, 1H); 5.50 ppm (s, 1H); 3.37–3.30 ppm (broad d, 6H); 2.03 ppm (s, 3H) (The compound is in the enol form immediately after dissolution in chloroform.)

$^{13}$C-NMR: 189.3 ppm; 173.4 ppm; 95.42 ppm; 95.35 ppm; 41.7 ppm (broad); 23.90 ppm (Conversion into the keto form was noted during integration taking a long time)

Elementary analysis: (calculated values for $C_6H_{11}ONS$)

|  | C | H | N | S |
|---|---|---|---|---|
| Calculated, % | 49.62 | 7.63 | 9.64 | 22.08 |
| Found, % | 49.68 | 7.73 | 9.66 | 21.94 |

FIG. 1 is an ORTEP diagram of this compound depicted according to the results of the X-ray crystallograhic analysis.

EXAMPLE 2

The reaction of bis(trimethylsilyl)thioketene and N,N-dimethyl acetamide was carried out in the same manner as in Example 1 and the solidified reaction mixture obtained after 48 hours of standing was dissolved as such in 4 ml of methyl alcohol containing 0.01% by weight of hydrogen chloride. Thereafter, the methyl alcohol solution was freed from volatile matters under reduced pressure and the solid residue was purified by sublimation to give 0.16 g of N,N-dimethyl-3-oxothiobutyramide. The overall yield of this product was 45% of the theoretical value based on the starting reactants.

EXAMPLE 3

The addition reaction of 0.50 g of bis(trimethylsilyl)thioketene and an amide compound was performed in substantially the same manner as in Example 1 excepting replacement of 0.24 g of N,N-dimethyl acetamide with 0.25 g (2.5 mmoles) of N,N-dimethyl propionamide and the reaction temperature was increased to 40° C. After standing for 7 days to effect the reaction, the reaction mixture was distilled under reduced pressure to give 0.36 g of the addition product as the intermediate, which could be identified to be the compound of the formula (IV) or (IV'), in which $R^1$, $R^2$ and R were each a methyl group and $R^s$ was an ethyl group, having a molecular formula of $C_{13}H_{29}ONSSi_2$ from the results of the elementary analysis shown below which were in good coincidence with the calculated values. The above mentioned yield of the intermediate was 48% of the theoretical value.

Elementary analysis:

|  | C | H | N | S |
|---|---|---|---|---|
| Calculated, % | 51.43 | 9.63 | 4.61 | 10.56 |
| Found, % | 51.12 | 9.57 | 4.65 | 10.66 |

In the next place, 0.22 g of this intermediate compound was dissolved in 5 ml of methyl alcohol containing 0.01% by weight of hydrogen chloride to form a solution which was, after standing for 48 hours at room temperature, freed from volatile matters under reduced pressure to leave 0.11 g of a crystalline solid which could be identified to be N,N-dimethyl-3-oxothiopentanamide of the formula $Me_2N\text{-}CS\text{-}CH_2\text{-}CO\text{-}Et$, in which Me is a methyl group and Et is an ethyl group, from the results of the elementary analysis shown below. The above mentioned yield of this product was 97.6% based on the intermediate and the overall yield was 47% based on the starting reactants relative to the theoretical values.

Elementary analysis: (calculated values for $C_7H_{13}ONS$)

|  | C | H | N | S |
|---|---|---|---|---|
| Calculated, % | 52.79 | 8.23 | 8.80 | 20.14 |
| Found, % | 52.61 | 8.26 | 8.85 | 19.89 |

EXAMPLE 4

A mixture consisting of 0.69 g (3.4 mmoles) of bis(trimethylsilyl)thioketene and 0.37 g (2.5 mmoles) of N,N-dimethyl benzamide was kept standing at 40° C. for 20 days and then distilled at 150° C. under a reduced pressure of 0.08 mmHg to give a viscous fluid which was dissolved in 5 ml of methyl alcohol containing 0.01% by weight of hydrogen chloride. After standing at room temperature for 48 hours, the solution was freed from volatile matters under reduced pressure and the residue was distilled at 152° C. under a reduced pressure of 0.1 mmHg to give 0.33 g of a viscous liquid product which could be identified from the results of the elementary analysis shown below to be N,N-dimethyl-3-oxo-3-phenylthiopropionamide of the formula $Me_2N\text{-}CS\text{-}CH_2\text{-}CO\text{-}Ph$, in which Me is a methyl group and Ph is a phenyl group. The yield of this product was 64% of the theoretical value based on the N,N-dimethyl benzamide.

Elementary analysis: (calculated values for $C_{11}H_{13}ONS$)

|  | C | H | N | S |
|---|---|---|---|---|
| Calculated, % | 63.74 | 6.32 | 6.76 | 15.47 |
| Found, % | 63.44 | 6.36 | 6.76 | 15.70 |

EXAMPLE 3

The addition reaction of 0.50 g of bis(trimethylsilyl)thioketene and an amide compound was performed in substantially the same manner as in Example 1 excepting replacement of 0.24 g of N,N-dimethyl acetamide with 0.28 g (2.8 mmoles) of 1-methylpyrrolidin-2-one. After standing for 4 days to effect the reaction, the reaction mixture was found to be in the form of a crystalline solid which was purified by sublimation at 85° C. under a reduced pressure of 0.05 mmHg to give 0.42 g of a crystalline solid as the intermediate compound. This compound could be identified to be the compound of the formula (IV) or (IV'), in which $R^2$ and R were each a methyl group and $R^1$ and $R^3$ jointly formed a divalent group of $-CH_2CH_2CH_2-$ forming a cyclic structure, having a molecular formula of $C_{13}H_{27}ONSSi_2$ from the results of the elementary analysis which were in good coincidence with the calculated values. The above mentioned yield of the intermediate was 56% of the theoretical value.

Elementary analysis:

|  | C | H | N | S |
|---|---|---|---|---|
| Calculated, % | 51.77 | 9.02 | 4.64 | 10.63 |
| Found, % | 51.92 | 9.02 | 4.65 | 10.39 |

In the next place, 0.12 g of this intermediate compound was dissolved in 2 ml of methyl alcohol containing 0.01% by weight of hydrogen chloride to form a solution which was, after standing for 4 hours at room temperature, freed from volatile matter under reduced pressure to leave 0.061 g of a crystalline solid which could be identified to be N-methyl-3-oxo-ε-thiocaprolactam of the formula

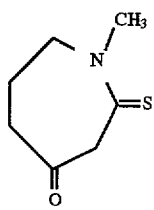

from the results of the elementary analysis shown below for the compound after purification by sublimation. The above mentioned yield of this product was 97% based on the intermediate and the overall yield was 54% based on the starting reactants relative to the theoretical values.

Elementary analysis: (calculated values for $C_7H_{11}ONS$)

|  | C | H | N | S |
|---|---|---|---|---|
| Calculated, % | 53.47 | 7.05 | 8.91 | 20.39 |
| Found, % | 53.78 | 7.17 | 8.99 | 20.03 |

EXAMPLE 6

The addition reaction of 0.50 g of bis(trimethylsilyl) thioketene and an amide compound was performed in substantially the same manner as in Example 1 excepting replacement of 0.24 g of N,N-dimethyl acetamide with 0.32 g (2.5 mmoles) of N-methyl-ε-caprolactam. After standing for 4 days at room temperature to effect the reaction, the reaction mixture was distilled at 130° C. under a reduced pressure of 0.15 mmHg to give 0.52 g of a viscous fluid as the intermediate compound. This compound could be identified to be the compound of the formula (IV) or (IV'), in which $R^2$ and R were each a methyl group and $R^1$ and $R^2$ jointly formed a divalent group of —$CH_2CH_2CH_2CH_2CH_2$— forming a cyclic structure, having a molecular formula of $C_{15}H_{31}ONSSi_2$ from the results of the elementary analysis which were in good coincidence with the calculated values. The above mentioned yield of the intermediate was 63% of the theoretical value.

Elementary analysis:

|  | C | H | N | S |
|---|---|---|---|---|
| Calculated, % | 54.65 | 9.48 | 4.25 | 9.73 |
| Found, % | 54.63 | 9.50 | 4.24 | 9.79 |

In the next place, 0.19 g of this intermediate compound was dissolved in 2 ml of methyl alcohol containing 0.01% by weight of hydrogen chloride to form a solution which was, after standing for 48 hours at room temperature, freed from volatile matters under reduced pressure to leave 0.10 g of a crystalline solid which could be identified to be 1-aza-1-methyl-2-thioxo-4-cyclononanone of the formula

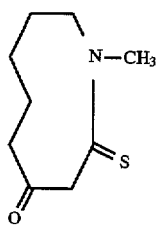

from the results of the elementary analysis shown below for the compound after purification by sublimation. The above mentioned yield of this product was 97% based on the intermediate and the overall yield was 61% based on the starting reactants relative to the theoretical values.

Elementary analysis: (calculated values for $C_9H_{15}ONS$)

|  | C | H | N | S |
|---|---|---|---|---|
| Calculated, % | 58.34 | 8.16 | 7.56 | 17.31 |
| Found, % | 58.59 | 8.21 | 7.549 | 17.21 |

What is claimed is:
1. A method for the preparation of an N,N-disubstituted β-ketothioamide compound represented by the general formula

$$R^1R^2N—CS—C_2—CO—R^3,$$

in which $R^1$ and $R^2$ are each a monovalent hydrocarbon group or each a divalent hydrocarbon group jointly forming a cyclic structure together with the nitrogen atom and $R^3$ is a hydrogen atom, a monovalent hydrocarbon group or a divalent hydrocarbon group forming a cyclic structure jointly with $R^1$, $R^1$ being a divalent hydrocarbon group and $R^2$ being a monovalent hydrocarbon group, which comprises the steps of:

(a) mixing an N,N-disubstituted amide compound represented by the general formula $$R^1R^2N—CO—R^3,$$

in which each symbol has the same meaning as defined above, and a bis(trialkylsilyl)thioketene compound represented by the general formula $$(R_3Si)_2C=C=S,$$

in which each R is, independently from the others, an alkyl group, to effect an addition reaction therebetween forming an intermediate compound; and (b) dissolving the intermediate compound obtained in step (a) in an alcohol.

2. The method for the preparation of an N,N-disubstituted β-ketothioamide compound as claimed in claim 1 in which the alkyl group denoted by R in the general formula representing the bis(trialkylsilyl)thioketene is a methyl group.

3. The method for the preparation of an N,N-disubstituted β-ketothioamide compound as claimed in claim 1 in which the alcohol used in step (b) is methyl alcohol.

4. The method for the preparation of an N,N-disubstituted β-ketothioamide compound as claimed in claim 1 in which the alcohol used in step (b) contains an acid.

5. The method for the preparation of an N,N-disubstituted β-ketothioamide compound as claimed in claim 4 in which the acid is hydrogen chloride.

6. The method for the preparation of an N,N-disubstituted β-ketothioamide compound as claimed in claim 5 in which the concentration of the hydrogen chloride in the alcohol is in the range from 0.005 to 0.05% by weight.

* * * * *